United States Patent
Watanabe et al.

(10) Patent No.: US 9,249,429 B2
(45) Date of Patent: Feb. 2, 2016

(54) MICROORGANISM HAVING HIGH SQUALENE-PRODUCING ABILITY, AND METHOD FOR PRODUCING SQUALENE BY MEANS OF SAME

(75) Inventors: Makoto Watanabe, Ibaraki (JP); Kunimitsu Kaya, Ibaraki (JP); Makato Shiho, Ibaraki (JP); Atsushi Nakazawa, Ibaraki (JP); Isao Inoue, Ibaraki (JP); Daisuke Honda, Hyogo (JP)

(73) Assignees: University of Tsukuba, Ibaraki (JP); Konan Gakuen, Hyogo (JP)

( * ) Notice: Subject to any disclaimer, the term of this patent is extended or adjusted under 35 U.S.C. 154(b) by 54 days.

(21) Appl. No.: 13/992,638

(22) PCT Filed: Dec. 9, 2011

(86) PCT No.: PCT/JP2011/078603
§ 371 (c)(1),
(2), (4) Date: Jul. 8, 2013

(87) PCT Pub. No.: WO2012/077799
PCT Pub. Date: Jun. 14, 2012

(65) Prior Publication Data
US 2013/0288327 A1    Oct. 31, 2013

(30) Foreign Application Priority Data
Dec. 9, 2010 (JP) ................................. 2010-275109

(51) Int. Cl.
*C12P 5/02* (2006.01)
*C12R 1/89* (2006.01)

(52) U.S. Cl.
CPC .. *C12P 5/026* (2013.01); *C12R 1/89* (2013.01)

(58) Field of Classification Search
None
See application file for complete search history.

(56) References Cited

PUBLICATIONS

Yokoyama et al. 2007. Taxonomic rearrangement of the genus *Schizochytrium* sensu lato based on morphology, chemotaxonomic characteristics, and 18S rRNA gene phylogeny (Thraustochytriaceae, Labyrinthulomycetes): emendation for *Schizochytrium* and erection of Aurantiochytrium and Oblongichytrium gen. nov. Mycoscience , vol. 48, pp. 199-211.*

Chen at al., "Optimization of nitrogen source for enhanced production of squalene from thraustochytrid Arantiochytrium sp.," New Biotechnol., Sep. 2010, vol. 27, No. 4, pp. 382-389.

Fan et al., "Enhanced production of squalene in the thraustochytrid Auranntiochytrium mangrovei by medium optimization and treatment with terbinafine," World J. Microbiol. Biotechnol., 2010, vol. 26, pp. 1303-1309.

Jiang et al., "Fatty acid composition and squalene content of the marine microalgae Schizochytrium mangrovei.," J. Agric. Food Chem., 2004, vol. 52, pp. 1196-1200.

Li et al., "Screening and characterization of squalene-producing thraustochytrids from Hong Kong mangroves," J. Agric. Food Chem., 2009, vol. 57, pp. 4267-4272.

Fan et al., "Lipid characterization of mangrove thraustochytrid-Schizochytrium mangrovei," J. Agric. Food Chem., 2007, vol. 55, pp. 2905-2910.

Kaya et al., "Thraustochytrid Aurantiochytnum sp. 18W-13a accumulates high amounts of squalene," Biosci. Biotechnol. Biochem., Nov. 7, 2011 (publishsed online), vol. 75, No. 11, pp. 2246-2248, retrieved from the internet on Dec. 26, 2011.

Nakazawa et al., "Optimization of culture conditions of the thraustochyrid Aurantiochytrium sp. strain 18W-13a for squalene production," Bioresour. Technol., 2012, pp. 287-291, (published online) retrieved from the internet on Dec. 26, 2011.

International Search Report dated Jan. 10, 2012 from PCT/JP2011/078603, filed Dec. 9, 2011.

Nakazawa et al., J. Appl. Phycol. (2014) 26: 29-41.

* cited by examiner

*Primary Examiner* — Debbie K Ware
*Assistant Examiner* — Kailash C Srivastava
(74) *Attorney, Agent, or Firm* — Kenyon & Kenyon LLP

(57) ABSTRACT

Provided is a strain belonging to the genus *Aurantiochytrium*, the strain being characterized by there being at least 10 mass % of squalene in all the lipids produced by the strain, and by forming colonies exhibiting an orange-to-red color.

2 Claims, 2 Drawing Sheets

SOLVENT: n-HEXANE/CHLOROFORM (9/1, v/v)
PLATE: SILICA GEL G

SAMPLE
1. n-HEXANE ELUATE FROM COLUMM
2. n-HEXANE/CHLOROFORM (9/1, v/v)
3. n-HEXANE/CHLOROFORM (1/1, v/v)

MICROORGANISM HAVING HIGH SQUALENE-PRODUCING ABILITY, AND METHOD FOR PRODUCING SQUALENE BY MEANS OF SAME

CROSS REFERENCE TO RELATED APPLICATIONS

This is a U.S. national phase of international application, PCT/JP2011/078603, filed on Dec. 9, 2011, which claims priority to Japanese application, JP 2010-275109, filed on Dec. 9, 2010.

TECHNICAL FIELD

The present invention relates to a novel microorganism having high squalene-producing ability, and to a method for producing squalene using the microorganism.

Squalene is an intermediate of sterol synthesis that has long been used throughout the world as a health food. In recent years, squalene has been found to have physiological activity, and its effects of preventing radiation-induced damage and preventing canceration of cells have become a topic of interest. Squalane, which is the reduced form of squalene, is also widely used as a humectant for cosmetics, and even as a mechanical lubricant oil and heat exchange medium.

The major sources of squalene are deep-sea sharks, and in the conventional methods of extracting and purifying squalene, deep-sea shark livers are collected, the cells are pulverized in hot water, and the resulting freed oily fat is collected and purified with an adsorbent or the like. However, shark catches are extremely unstable since they are captured from the wild, and therefore prices vary due to unstable supply. In recent years, restrictions have been placed on capturing of deep-sea sharks since they have been designated as an endangered species, and from the viewpoint of protecting the natural environment, it has been desirable to develop an alternative method for producing squalene other than by extraction from deep-sea sharks.

Alternative methods known for producing squalene include extraction of squalene from plant sources such as wheat germ, rice bran oil and olive oil, and in the case of olive oil, for example, the squalene content is low and the proportion of squalene-related impurities is high, while quality evaluation is inferior to that of shark squalene, such that numerous problems have been associated with commercial production.

A demand therefore exists for a method of producing squalene that can provide stable squalene without converting other natural oils, thus production of squalene from microorganisms has been proposed. For example, it has been reported that a maximum of 49.4 mg of squalene is produced per 1 liter of culture solution from protozoans belonging to the genus *Euglena* (Patent Literature 1: Japanese Unexamined Patent Publication HEI No. 7-115981). The amount of production per dry weight is unknown, but the squalene content of the total produced lipids under maximum content lipid production conditions remains about 30%. In addition, while it has been reported that squalene was obtained at a maximum of 29.176 mg/g (dry cells) of microorganisms belonging to the genus *Fusarium*, it was necessary to induce mutations in specific microorganisms (Patent Literature 2: Japanese Unexamined Patent Publication HEI No. 5-90). It has also been reported that squalene was obtained at a maximum of 155.3 mg/g (dry cells) from yeast or the like, but mutations must be induced to accumulate squalene within the cell, and a sterol must be added to the medium (Patent Literature 3: Japanese Patent No. 2663039).

For industrial use, however, it is preferred to accomplish production of squalene in large amounts with an inexpensive medium and apparatus, without requiring strict control.

CITATION LIST

Patent Literature

[Patent Literature 1] Japanese Unexamined Patent Publication HEI No. 7-115981
[Patent Literature 2] Japanese Unexamined Patent Publication HEI No. 5-90
[Patent Literature 3] Japanese Patent No. 2663039

DISCLOSURE OF THE INVENTION

Problems to be Solved by the Invention

It is an object of the invention to provide squalene at a high yield, without requiring induced mutations or culturing under special conditions.

Means for Solving the Problems

As a result of much research in light of the demand described above, the present inventors have discovered a microorganism with excellent proliferative ability, and capable of producing squalene in large amounts. It was also found that the microorganism can be used to efficiently produce squalene, whereupon the invention was completed.

The present invention provides a novel strain belonging to the order Labyrinthulales, family Thraustochytriaceae, genus *Aurantiochytrium*, having the ability to produce squalene, the strain producing at least 10% by weight of squalene among the total lipids, and forming colonies that exhibit an orange-to-red color. The invention also provides a method for producing squalene wherein the new strain of *Aurantiochytrium* is cultured in culture medium and squalene produced by the proliferated strain is harvested. The invention still further provides use of the new strain of *Aurantiochytrium* for production of squalene.

MODE FOR CARRYING OUT THE INVENTION

The microorganism with high squalene-producing ability according to the invention may be any one that is a microorganism belonging to the genus *Aurantiochytrium*, having squalene-producing ability and exhibiting an orange-to-red color (approximately 590-750 nm as the maximum absorption wavelength). Specifically, there may be used the strain *Aurantiochytrium* tsukuba-3, for example, which is a novel microorganism of the invention.

1. Novel Strain of the Invention

The novel strain of the invention was harvested and separated from leaves of mangrove growing on the coasts of Okinawa Prefecture, Japan. The strain has the following characteristics.

The *Aurantiochytrium* strain of the invention normally does not form distinct colonies.

Figure 1:
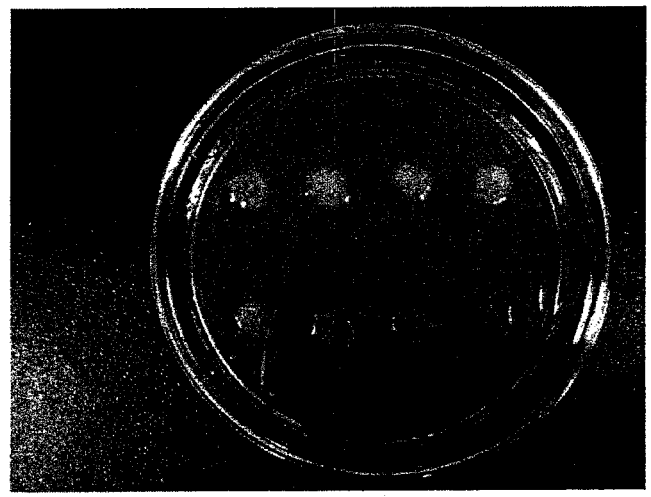
FIG. 1 is a photograph of *Aurantiochytrium* tsukuba-3 according to the invention, cultured in agar medium.

External morphology: The *Aurantiochytrium* strain of the invention cultured in agar medium can exhibit an orange-to-red color (FIG. 1).

Figure 2:
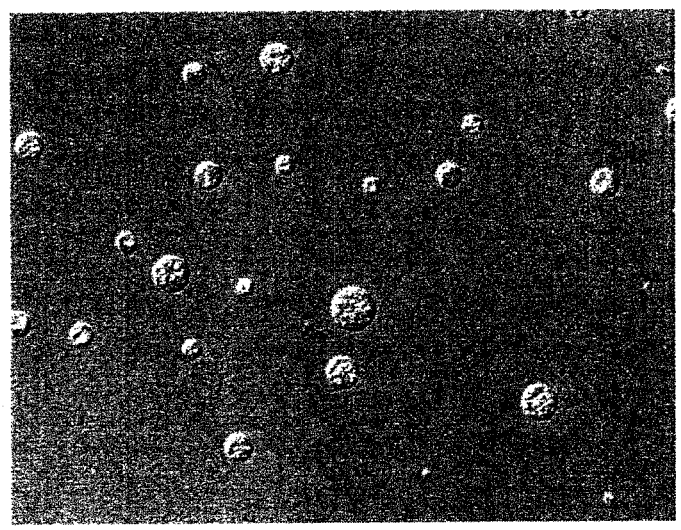
FIG. 2 is a photograph of cells of *Aurantiochytrium* tsukuba-3 according to the invention.
Figure 3:
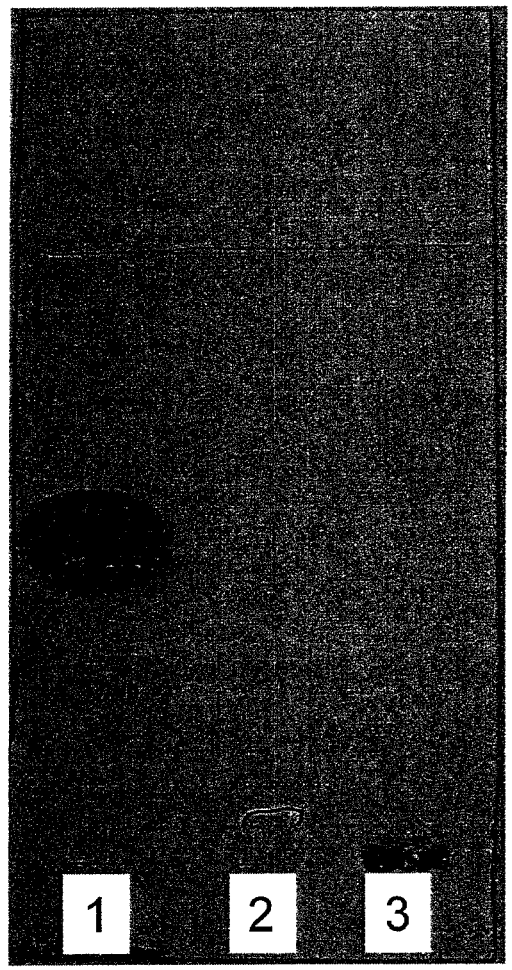
FIG. 3 is an analytical photograph of lipids produced by *Aurantiochytrium* tsukuba-3 according to the invention, on thin-layer silica gel after silica gel column purification.

Cellular morphology: The morphology is spherical, with sizes of approximately 5 to 15 µm (FIG. 2).

The vegetative cells may be basically spherical and non-motile. In the initial logarithmic growth stage of the culture, motile cells with flagella are often seen, but absolutely no motile cells are observed in the resting stage, and this may result in only spherical vegetative cells.

The *Aurantiochytrium* strain of the invention belongs to the order Labyrinthulales, family Thraustochytriaceae, genus *Aurantiochytrium*, is heterotrophic, and it abundantly accumulates squalene in the cells. Labyrinthulomycetes relate to oomycetes, so phylogenetically their lineage is separate from anthentic fungi and related to heterokont plants such as brown algae and diatoms, and together with heterokont plants, they form the lineage of Stramenopila. Previously known strains of this family include a strain having the property of abundantly accumulating higher unsaturated fatty acids such as docosahexaenoic acid (DHA) and eicosapentaenoic acid (EPA) (strain SR21, Japanese Patent No. 2764572). Squalene-producing strains exist, but the known ones are only able to produce up to a maximum of about 0.3 to 0.6 mg/g (dry cells) (G. Chen. et al. New Biotechnology 27, 382-289 (2010); Q. Li et al., J. Agric. Food Chem. 57(10), 4267-4272 (2009); and K. W. Fan et al., World J. Microbiol. Biotechnol. 26, 1303-1309 (2010)).

The *Aurantiochytrium* tsukuba-3 strain of the invention has been deposited in Japan at the International Patent Organism Depositary (IPOD) of the National Institute of Advanced Industrial Science and Technology (Tsukuba Central 6, 1-1, Higashi 1-chome, Tsukuba-shi, Ibaraki-ken, Japan 305-8566) on Dec. 9, 2010, as FERM P-22047. It was then transferred to an international depository under the Budapest Treaty on Dec. 8, 2011, and assigned the designation FERM BP-11442.

The microorganism to be used for the method for producing squalene according to the invention is not limited to *Aurantiochytrium* tsukuba-3 strain mentioned above, and may be any strain that has essentially the same microbial properties as the aforementioned *Aurantiochytrium* strain. After the microorganism is cultured and the squalene-containing lipids have been accumulated at high concentration in the cultured cells, the squalene-containing lipids are harvested, and squalene may be produced by extracting the squalene by a known method.

2. Culturing Conditions

Growth of the novel strain of *Aurantiochytrium* according to the invention is carried out by seeding the strain into suitable culture medium prepared with natural sea water or artificial seawater, and culturing it by an established method. The culture medium used may be any known one, with carbon sources that are carbohydrates such as glucose, fructose, saccharose and starch, as well as fat or oils such as oleic acid and soybean oil, and glycerol, sodium acetate and the like. These carbon sources are used, for example, at concentrations of 20 to 120 g per liter of culture medium. The nitrogen source may be organic nitrogen such as yeast extract, corn steep liquor, polypeptone, sodium glutamate or urea, inorganic nitrogen such as ammonium acetate, ammonium sulfate, ammonium chloride, sodium nitrate or ammonium nitrate, or protein digest. Potassium phosphate and the like may be used in appropriate combinations as inorganic salts. The culture medium may also contain appropriate vitamins, protease peptone, yeast extract and the like. The proportion of natural water or artificial seawater in the culture solution is approximately 50% by volume. After preparation, the culture medium may have its pH adjusted by addition of an appropriate acid or base. The pH of the culture medium is pH 2.0-11.0, preferably pH 3.0-10.0, more preferably pH 4.0-9.0 and more preferably pH 4.5-9.0, and usually a pH of 6.5 is used. Before adding the solution containing the novel strain of *Aurantiochytrium* to the culture medium, the culture medium is sterilized with an autoclave. The culturing is carried out at a culturing temperature of 5° C. to 40° C., preferably 10° C. to 35° C. and more preferably 10° C. to 30° C., usually for 1 to 10 days and preferably 3 to 7 days. The culturing may be carried out by aeration culture, shake culture or batch culture, but preferably the culturing is by aeration culture or shake culture.

3. Squalene Extraction and Analysis

The squalene-containing lipid produced by the novel strain of *Aurantiochytrium* according to the invention may be extracted and analyzed by a method known to those skilled in the art. For example, the wet cells obtained by culturing and growth as described above and concentrated from the obtained culture by centrifugal separation or filtration, are dried by freeze-drying or heated drying. Alternatively, the cultured cells aliquot may be directly used in a squalene-containing lipid extraction step.

An organic solvent may be used to extract the lipids from the obtained dry cells, or from the cultured cell aliquot. The extraction may be conducted two or more times using different organic solvents. The organic solvent used may be a liquid mixture of a polar solvent and a weakly polar solvent, such as a chloroform/methanol mixed solvent (for example, 1:1 or 1:2) or an ethanol/diethyl ether mixed solvent. Following extraction, n-hexane is used for extraction from a sample obtained by concentrated drying under a nitrogen stream, for example. The obtained extract is purified by a method known to those skilled in the art. For example, silica gel or acidic white clay may be used to adsorb and purify the polar lipids. The purified squalene is then analyzed by NMR, IR, gas chromatography or GC/MS.

The novel strain of *Aurantiochytrium* according to the invention, obtained by the procedure described above, is produced at a biomass of at least 1 g, preferably at least 3 g, and preferably 5 g to 7 g, as the dry cell mass per liter of culture medium. Also, the time required to reach this biomass is 1 to 10 days, preferably 2 to 8 days and more preferably 3 to 7 days.

The total lipid content produced by the novel strain of *Aurantiochytrium* according to the invention is at least 5% of cell dry weight, preferably at least 25% of cell dry weight and more preferably at least 30% of cell dry weight, per gram of dry cell mass. The "lipids" referred to here include squalene and sterols, and/or triglycerides that include components such as pigments, or conjugated lipids. The squalene among the total lipid produced by the novel strain of *Aurantiochytrium* according to the invention constitutes at least 10% of cell dry weight, at least 30% of cell dry weight, at least 50% of cell dry weight, preferably 10 to 100% of cell dry weight or 30 to 95% of cell dry weight, more preferably 50 to 90% of cell dry weight and most preferably 60 to 85% of cell dry weight.

Thus, the amount of squalene production per liter is 1.0 to 2.0 g.

When the novel strain of *Aurantiochytrium* according to the invention is used, squalene is present at high concentration in the produced lipids. This is clearly more than 500-fold productivity for squalene, compared to previously reported squalene-producing *Aurantiochytrium* strains.

In addition, the novel strain of *Aurantiochytrium* according to the invention is characterized by exceedingly rapid growth. With 3 to 12 cell divisions being observed per day, it has a much faster growth rate than *Euglena* or *Chlorella*, and it has a growth speed of at least 10 to 30 times that of hydrocarbon-producing *Botryococcus*.

As mentioned above, the novel strain of *Aurantiochytrium* according to the invention is a strain suitable for mass production, requiring no induced mutations or culturing under special conditions, and capable of providing squalene at high yield in a short period of time.

Examples of analyzing squalene isolated and produced by the novel strain of *Aurantiochytrium* according to the invention will now be provided, with the understanding that the claims of the invention are not limited by these examples.

EXAMPLE 1

1. Culturing and Isolation

After adding seawater (500 ml per 1 L of culture medium) and distilled water to GPY culture medium (20 g of glucose, 10 g of polypeptone and 5 g of yeast extract per 1 L of culture medium), it was combined with solution containing the *Aurantiochytrium* strain of the invention, to a volume of 1 L (pH 6.5). This was autoclaved at 120° C. for 20 minutes, and then shake culturing was carried out at 25° C. for 4 days, under aerated conditions.

2. Analysis of Produced Lipids

To the culture solution containing the obtained *Aurantiochytrium* strain of the invention there was added chloroform/methanol (2:1, V/V) for extraction of the lipids, and after concentration to dryness, extraction was again performed with n-hexane.

The sample was purified by column chromatography. The conditions were as follows: column inner diameter: 10 φmm, silica gel: 20 ml (packed column volume), solvent: (1) n-hexane, (2) n-hexane/chloroform (9/1), (3) n-hexane/chloroform (1/1), (4) chloroform, (5) chloroform/methanol (1/1), (6) chloroform/methanol (1/4). The obtained eluate was analyzed with an n-hexane/chloroform (9/1) solvent, using a silica gel G plate, and a simple substance was confirmed to be present in the n-hexane eluate from the elution of (1) above (FIG. 2). The substance was subjected to TOF/MS analysis.

TOF/MS analysis confirmed that the simple substance was a hydrocarbon with the molecular formula $C_{30}H_{50}$ (degree of unsaturation: 6) ((M+H) observed exact mass: 411.3987, Formula (M+H): $C_{30}H_{51}$, calcd for C30H51, 411.3985, 0.2 mmu). Further analysis by NMR confirmed it to be squalene having the following structure.

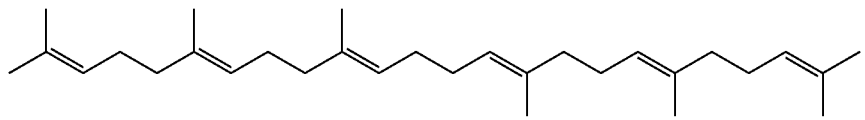 [SMILES: CC(C)=CCC/C(C)=C/CC/C(C)=C/CC/C=C(\C)CC/C=C(\C)CCC=C(C)C]

This strain, *Aurantiochytrium* tsukuba-3, was deposited in Japan at the International Patent Organism Depositary (IPOD) of the National Institute of Advanced Industrial Science and Technology (Tsukuba Central 6, 1-1, Higashi 1-chome, Tsukuba-shi, Ibaraki-ken, Japan 305-8566) (FERM P-22047). It was then transferred to an international depository under the Budapest Treaty on Dec. 8, 2011, and assigned deposit number FERM BP-11442.

The composition of the lipids obtained from strain *Aurantiochytrium* tsukuba-3 is shown in Table 1. As comparative examples there are shown the analysis results for other strains (A, B) belonging to the genus *Aurantiochytrium* and forming colonies exhibiting an orange-to-red color similar to strain *Aurantiochytrium* tsukuba-3 within the scope of the invention, for other strains belonging to the genus *Aurantiochytrium* (C, D and E) but not within the scope of the invention, and forming colonies exhibiting a white, cream-colored or yellow color, and for strain *Aurantiochytrium* SR21.

| Strain name | Total lipid content of dry cells (%) | Squalene (%) | Triglycerides* (%) | Complex lipids (%) | Colony color |
|---|---|---|---|---|---|
| tsukuba-3 | 22.6 | 69.8 | 14.3 | 15.9 | Orange-to-red |
| A | 26.5 | 65.2 | 19.6 | 15.2 | Orange-to-red |
| B | 26.0 | 21.8 | 35.2 | 33.0 | Orange-to-red |
| C | 25.2 | 0.2 | 84.2 | 15.7 | White-to-cream |
| D | 19.5 | 0.3 | 56.7 | 43.0 | White |
| E | 20.1 | 1.1 | 46.6 | 52.4 | Yellow |
| SR21 | 17.1 | 0.1 | 37.6 | 63.3 | White-to-cream |

*Triglycerides fraction include sterol esters and pigments.

DEPOSIT NUMBER

*Aurantiochytrium* tsukuba-3 FERM BP-11442

What is claimed is:

1. A method for producing squalene that employs a strain of *Aurantiochytrium* tsukuba-3 (deposit number: FERM BP-11442), wherein said strain produces at least 10 mass % squalene among the total lipids, and forming colonies that exhibit an orange-to-red color, said method comprising the steps of:

culturing cells of said strain at pH of 4.5-9.0 and 10° C. to 30° C. for 3 to 7 days;

harvesting squalene-containing lipids from said cultured cells; and then extracting squalene from said squalene-containing lipids.

2. The method of claim 1, wherein said culturing step is conducted in artificial sea water.